(12) United States Patent
Iguchi et al.

(10) Patent No.: US 10,858,328 B2
(45) Date of Patent: Dec. 8, 2020

(54) METHOD FOR PRODUCING ETHYLENE OXIDE

(71) Applicant: NIPPON SHOKUBAI CO., LTD., Osaka (JP)

(72) Inventors: Shingo Iguchi, Kawasaki (JP); Hideto Suzuki, Kawasaki (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 0 days.

(21) Appl. No.: 16/088,748

(22) PCT Filed: Mar. 30, 2017

(86) PCT No.: PCT/JP2017/013372
§ 371 (c)(1),
(2) Date: Sep. 26, 2018

(87) PCT Pub. No.: WO2017/170915
PCT Pub. Date: Oct. 5, 2017

(65) Prior Publication Data
US 2019/0077778 A1    Mar. 14, 2019

(30) Foreign Application Priority Data
Mar. 30, 2016   (JP) ................. 2016-069720

(51) Int. Cl.
| C07D 301/10 | (2006.01) |
| C07D 303/04 | (2006.01) |
| F28D 15/02  | (2006.01) |
| F28F 21/08  | (2006.01) |

(52) U.S. Cl.
CPC ......... C07D 301/10 (2013.01); C07D 303/04 (2013.01); F28D 15/02 (2013.01); F28F 21/083 (2013.01)

(58) Field of Classification Search
CPC .................................................. C07D 301/10
See application file for complete search history.

(56) References Cited

U.S. PATENT DOCUMENTS

| 8,073,486 B2 | 12/2011 | Mundarath et al. | |
| 2001/0003783 A1* | 6/2001 | McKay et al. ........ | C07C 51/252 562/512 |
| 2008/0182999 A1 | 7/2008 | Rekers et al. | |
| 2016/0052900 A1 | 2/2016 | Watanabe et al. | |
| 2017/0107188 A1 | 4/2017 | Kawaguchi et al. | |

FOREIGN PATENT DOCUMENTS

| GB | 0531256 A | 1/1941 |
| JP | 1985-131817 A | 7/1985 |
| JP | 1987-103072 A | 5/1987 |
| JP | 2001-220362 A | 8/2001 |
| JP | 2010-516657 A | 5/2010 |
| JP | 2013-209328 A | 10/2013 |
| JP | 2013209328 A * | 10/2013 |
| WO | WO 2014/157699 A1 | 10/2014 |
| WO | WO 2015/152298 A1 | 10/2015 |

OTHER PUBLICATIONS

English-language Machine translation of JP 2013-209328 A (published Oct. 2013), provided from J-PLAT-PAT at https://www.j-platpat.inpit.go.jp/h0200, accessed Aug. 16, 2019. (Year: 2013).*
NBK. "Stainless steel." (Dec. 14, 2016). Accessed Aug. 16, 2019. Available from: < https://www.nbk1560.com/~/media/Images/en/Product%20Site/en_technical/33_Stainless%20Steel.ashx?la=en >. (Year: 2016).*
WeatherQuestions.com. "What is the dewpoint temperature?" (Aug. 16, 2012). Accessed Aug. 16, 2019. Available from: < https://weatherstreet.com/weatherquestions/What_is_dewpoint_temperature.htm >. (Year: 2012).*
AquaLogic. "Learn How a Heat Exchanger Works." (Feb. 19, 2016). Accessed Aug. 16, 2019. Available from: < https://aqualogicinc.com/learn-how-a-heat-exchanger-works/ >. (Year: 2016).*
Kagaku Process—Kiso kara Gijutsu Kaihatso made—, 1st Edition, Kabushiki Kaishe Tokyo Kagaku Dojin, 1998, pp. 121 to 128.
International Search Report dated Jul. 11, 2017, which issued in PCT Application No. PCT/JP2017/013372, English Translation, including Eng. Translation.
Official Notice of Reasons for Refusal dated Jan. 28, 2020, which issued in the corresponding Japanese Patent Application No. 2016-069720, including English translation.

* cited by examiner

*Primary Examiner* — John S Kenyon
(74) *Attorney, Agent, or Firm* — Dickinson Wright PLLC

(57) ABSTRACT

According to the present invention, there is provided means for suppressing the occurrence of corrosion on the inner tube side in a heat exchanger and enabling continuous production for a long time period in a process for producing ethylene oxide.

An embodiment of the present invention relates to a method for producing ethylene oxide, the method including: supplying a raw material gas including ethylene, molecular oxygen, and a chlorine compound to an ethylene oxidation reactor; subjecting ethylene and molecular oxygen in the raw material gas to catalytic vapor phase oxidation in the ethylene oxidation reactor in the presence of a silver catalyst, and thereby producing a gas including ethylene oxide, water, and a chlorine compound; and cooling a gas to be cooled including water and the chlorine compound using a heat exchanger. According to this method, in the heat exchanger, the gas to be cooled including water to be cooled and a chlorine compound is cooled at a linear gas velocity on the heat exchanger inner tube side of 7 m/s or higher.

12 Claims, 3 Drawing Sheets

METHOD FOR PRODUCING ETHYLENE OXIDE

TECHNICAL FIELD

The present invention relates to a method for producing ethylene oxide.

BACKGROUND ART

Nowadays, ethylene oxide is produced by catalytic vapor phase oxidation of ethylene using a molecular oxygen-containing gas in the presence of a silver catalyst. A purification method in a process for producing ethylene oxide is approximately as follows (see JP 62-103072 A).

First, ethylene and a molecular oxygen-containing gas are subjected to catalytic vapor phase oxidation on a silver catalyst, and thereby a reaction product gas containing ethylene oxide is obtained (reaction step). Subsequently, the reaction product gas thus obtained is introduced into an ethylene oxide absorption column and is brought into contact with an absorption liquid containing water as a main component. Thereby, ethylene oxide is recovered as an aqueous solution (absorption step). Next, the aqueous solution of ethylene oxide thus recovered is fed to a purification system for ethylene oxide and passed through several stages, and high-purity ethylene oxide is obtained. This purification system for ethylene oxide usually includes a stripping step, a purification step, a dehydration step, a light fraction separation step, a heavy fraction separation step, and the like.

Meanwhile, in regard to an exhaust gas that is discharged from the column top of an ethylene oxide absorption column and contains unreacted ethylene, carbon dioxide gas (carbon dioxide; $CO_2$) and water as by-products, and inert gases (nitrogen, argon, methane, ethane, and the like), conventional treatment of the exhaust gas is carried out by directly circulating the exhaust gas into an ethylene oxidation process, or by extracting a portion thereof, introducing that portion into a carbon dioxide gas absorption column, selectively absorbing a carbon dioxide gas using an alkaline absorption liquid, supplying this absorption liquid to a carbon dioxide gas stripper column, and stripping and recovering a carbon dioxide gas therein (see JP 60-131817 A).

SUMMARY OF INVENTION

In the conventional production processes for ethylene oxide such as the production processes disclosed in JP 62-103072 A and JP 60-131817 A, it is common practice to provide a heat exchanger in order to heat and cool a raw material gas, a recycled gas, and the like in a reaction system where reactions are carried out, a carbon dioxide gas system where stripping and recovery of a carbon dioxide gas are carried out, and the like. However, in the conventional production processes for ethylene oxide, there is a problem that when production is carried out for a long time period, corrosion occurs on the heat exchanger inner tube side.

Thus, it is an object of the present invention to provide, for a production process for ethylene oxide, a means for suppressing corrosion in the heat exchanger inner tubes and enabling continuous production for a long time period.

The inventors of the present invention conducted a thorough investigation in an attempt to solve the problems described above. Generally, it is known that when a liquid containing a chlorine compound adheres to a metal surface that is left to stand, the metal surface is corroded. The inventors of the present invention recognized that corrosion occurs in the heat exchanger inner tubes similarly in the above-described processes, because the raw material gas includes a chlorine compound, and the gas to be cooled, which is cooled by the exchanger, includes a chlorine compound and water. The present inventors newly conducted an investigation, and as a result, they surprisingly found that when a gas to be cooled including water and a chlorine compound is cooled by passing the gas through the heat exchanger inner tube side, the problems described above can be addressed by adjusting the linear gas velocity to 7 m/s or higher. Thus, the inventors completed the present invention.

That is, an aspect of the present invention relates to a method for producing ethylene oxide. This production method includes supplying a raw material gas including ethylene, molecular oxygen, and a chlorine compound to an ethylene oxidation reactor; subjecting ethylene and molecular oxygen in the raw material gas to catalytic vapor phase oxidation in the presence of a silver catalyst in the ethylene oxidation reactor, and thereby producing a gas including ethylene oxide, water, and a chlorine compound; and cooling a gas to be cooled including water and the chlorine compound using a heat exchanger. This production method has a feature that a gas to be cooled including water and a chlorine compound is cooled in a heat exchanger at a linear gas velocity on the heat exchanger inner tube side of 7 m/s or higher.

BRIEF DESCRIPTION OF DRAWINGS

FIG. 2 corresponds to a stripping step that will be described below.

DESCRIPTION OF EMBODIMENTS

Hereinafter, embodiments for carrying out the present invention will be described with reference to the drawings as appropriate. However, the present invention is not intended to be limited only to the following embodiments. Furthermore, the dimensional ratios of the drawings are exaggerated for the convenience of explanation and may be different from the actual ratios.

In the present specification, the expression "X to Y" representing a range implies "more than or equal to X and less than or equal to Y".

An embodiment of the present invention is a method for producing ethylene oxide, the method including supplying a raw material gas including ethylene, molecular oxygen, and a chlorine compound to an ethylene oxidation reactor; subjecting ethylene and molecular oxygen in the raw material gas to catalytic vapor phase oxidation in the presence of a silver catalyst in the ethylene oxidation reactor, and thereby producing a gas including ethylene oxide, water, and a chlorine compound; and cooling a gas to be cooled including water and the chlorine compound using a heat exchanger, and in this production method, the gas to be cooled including water and a chlorine compound is cooled in the heat exchanger at a linear gas velocity on the heat exchanger inner tube side of 7 m/s or higher. According to the production method related to the present embodiment, corrosion of the heat exchanger inner tube is suppressed, and continuous production for a long time period is enabled, in a production process for ethylene oxide. The production process for ethylene oxide according to the present invention can provide a very advantageous effect from an industrial viewpoint, that since the replacement frequency for heat exchangers can be remarkably decreased, the production efficiency can be increased.

The raw material gas includes ethylene, molecular oxygen, and a chlorine compound as essential components. Furthermore, the raw material gas may also have nitrogen, helium, argon, carbon dioxide, steam, and one kind or two or more kinds of lower hydrocarbons such as methane and ethane incorporated therein. The composition of the raw material gas is not particularly limited; however, for example, a mixed gas including, on the basis of the mass of the raw material gas, 0.5% to 40% by mass, and preferably 10% to 30% by mass, of ethylene; 5% to 15% by mass, and preferably 9% to 12% by mass, of oxygen (for example, a molecular oxygen gas); and 0.5% to 30% by mass, and preferably 8% to 13% by mass, of a carbon dioxide gas; with the balance being steam, inert gases such as nitrogen, argon, or lower hydrocarbons, and also including 0.01 to 1,000 ppm by volume of a chlorine compound based on the volume of the raw material gas, may be used.

The chlorine compound is a compound that functions as a reaction regulator and exists as a gas at least in the reactor. The chlorine compound is preferably an organic chlorine compound, and examples include chlorinated alkanes having 1 to 6 carbon atoms, chlorinated alkenes having 1 to 6 carbon atoms, and chlorinated benzene, such as vinyl chloride, chloroform, chlorinated biphenyl, monochlorobenzene, methyl chloride, t-butyl chloride, dichloromethane, dichloroethylene, trichloroethylene, dichloropropane, dichloropropene, chlorobutane, dichlorobutane, chlorobutene and the like. These compounds can be used singly or in combination of two or more kinds thereof. Among these, it is preferable to use chlorinated ethylene. The concentration of such a chlorine compound in the raw material gas is preferably 0.01 to 1,000 ppm by volume, more preferably 0.1 to 100 ppm by volume, and particularly preferably 0.5 to 50 ppm by volume, based on the volume of the raw material gas.

According to the method for producing ethylene oxide according to an embodiment of the present invention, it is essential to use a heat exchanger in order to cool a gas including water and a chlorine compound.

The position of installation of the heat exchanger for cooling a gas to be cooled including water and a chlorine compound is not particularly limited, and the heat exchanger may be installed at any position of the ethylene oxide production process. The heat exchanger in which the linear gas velocity on the heat exchanger inner tube side is adjusted to 7 m/s or higher, is preferably one heat exchanger or two or more heat exchangers that are disposed within a system for producing ethylene oxide by an oxidation reaction of ethylene as will be described below (in the present specification, also simply referred to as "reaction system"), or one heat exchanger or two or more heat exchangers that are disposed within a carbon dioxide gas recovery system, which may be optionally included and begins from the introduction of a gas into the carbon dioxide gas absorption column (in the present specification, also simply referred to as "carbon dioxide gas system"). It is preferable that the heat exchanger refers to one or two or more heat exchangers disposed in the reaction system and one or two or more heat exchangers disposed in the carbon dioxide gas system, and it is more preferable that the heat exchanger refers to all the heat exchangers existing in the production system, which are intended for cooling a gas to be cooled including water and a chlorine compound.

In regard to the heat exchanger for cooling a gas to be cooled including water and a chlorine compound, there are no particular limitations on the specific structure, and the heat exchanger may be any apparatus capable of heat exchange between the gas to be cooled including water and a chlorine compound and a heat-absorbing medium. From this point of view, any known heat exchanger can be used as the heat exchanger. Among these, it is preferable to use a multitubular heat exchanger. Usually, a multitubular heat exchanger has a structure in which tubular bundles obtained by binding a large number of fine heat transfer tubes having a small thickness (hereinafter, also referred to as inner tubes) into one bundle is disposed inside a cylindrical body, and the multitubular heat exchanger implements heat exchange between a thermal medium and a heat-absorbing medium, which are brought into contact with the inside and the outside of inner tubes. Generally, in order to make the flow of the body side fluid to flow most effectively in the inner tubes, to enhance the heat transfer efficiency, and to support the inner tubes, baffle plates are provided.

Regarding the heat exchanger, any of a vertical heat exchanger and a horizontal heat exchanger may be used. From the viewpoint of corrosion prevention, a vertical heat exchanger in which retention materials are not easily generated inside the inner tubes is preferred; however, from the viewpoint that the corrosion prevention effect of the present invention is more effectively utilized in a system where corrosion occurs more easily, a horizontal heat exchanger can be preferably used.

In a heat exchanger for cooling a gas to be cooled including water and a chlorine compound, the material that forms the heat exchanger inner tubes is not particularly limited; however, a stainless steel product is preferred. By employing stainless steel products as the inner tubes, corrosion occurring at the contact areas between the inner tubes and gases, or the generation of fissure called stress corrosion cracking can be reduced.

The type of the stainless steel that forms the heat exchanger inner tubes is not particularly limited, and known stainless steels such as martensitic stainless steel, ferritic stainless steel, austnitic stainless steel, and precipitation hardening type stainless steel can be used. Among these, materials that have been conventionally considered to possibly undergo corrosion during long-term production can also be preferably used, due to the corrosion prevention effect in long-term production that is provided by the present invention. That is, regarding the heat exchanger according to an embodiment of the present invention, from the viewpoint of more effectively utilizing the corrosion prevention effect of the present invention, a heat exchanger having heat exchanger inner tubes made of general stainless steel that are industrially used at relative low prices can also be preferably used. In addition, regarding the heat exchanger, it is definitely possible to use one having heat exchanger inner tubes made of a stainless steel having a special composition in order to increase corrosion prevention.

Here, regarding the stainless steel that forms the heat exchanger inner tubes, it is preferable to use a stainless steel in which the content (mass %) of chromium (Cr) and the content (mass %) of molybdenum (Mo) included therein with respect to the total mass of the stainless steel satisfy the following Formula 1:

[Mathematical Formula 1]

$$11 \leq \text{Content of chromium (mass \%)} + 2 \times \text{content of molybdenum (mass \%)} \leq 24 \quad \text{(Formula 1)}$$

The value of the above-described Formula 1 represents easy corrodibility of stainless steel, and a smaller value of Formula 1 implies that the stainless steel is more susceptible to corrosion. Therefore, it is implied that a stainless steel satisfying Formula 1 is preferable from the viewpoint that a heat exchanger having heat exchanger inner tubes made of a stainless steel that is more susceptible to corrosion can utilize the corrosion prevention effect of the present invention more effectively. From the same point of view, regarding the stainless steel that forms the heat exchanger inner tubes, the value of the following Formula 1 is more preferably 20 or less, and even more preferably 18 or less. The lower limit is a value preferable as a stainless steel for industrial use.

Examples of the stainless steel that satisfies Formula 1 include martensitic stainless steels such as SUS403, SUS410, SUS410J1, SUS410F2, SUS416, SUS420J1, SUS420J2, SUS420F, SUS420F2, SUS431, SUS440A, SUS440B, SUS440C, and SUS440F; ferritic stainless steels such as SUS405, SUS410L, SUS430, SUS430F, and SUS434; austnitic stainless steels such as SUS201, SUS202, SUS301, SUS302, SUS303, SUS303Se, SUS303Cu, SUS304, SUS304L, SUS304N1, SUS304N2, SUS304LN, SUS304J3, SUS305, SUS309S, SUS316, SUS316L, SUS316N, SUS316Ti, SUS890L, SUS321, SUS347, and SUSXM15J1; and precipitation hardening type stainless steels such as SUS630 and SUS631. Among these, from the viewpoint of achieving a balance between mass productivity and mechanical characteristics and the like, the stainless steel is preferably SUS430, SUS430F, SUS304, SUS304L, SUS304N1, SUS304N2, SUS304LN, SUS304J3, SUS316, SUS316L, SUS316N, or SUS316Ti; more preferably SUS430, SUS304, SUS316, or SUS316L; and even more preferably SUS430. These are described according to the JIS (Japan Industrial Standards).

Regarding the heat-absorbing medium, a heat-absorbing medium having a boiling point lower than that of the gas to be cooled including water and a chlorine compound, which is a heating medium supplied to the heat exchanger, having a boiling point higher than normal temperature, and having a high heat capacity, is suitably used. Furthermore, the heat-absorbing medium of the heat exchanger is not particularly limited; however, it is preferable that the heat-absorbing medium is a gas including ethylene, molecular oxygen, and a chlorine compound.

Here, the reaction product gas in the reaction system is preferably a gas including ethylene, molecular oxygen, and a chlorine compound in addition to ethylene oxide and water. At this time, a supplied gas in the carbon dioxide gas system that will be described below may include water and a chlorine compound, and the present invention can be applied to not only the heat exchanger in the reaction system but also to the heat exchanger in the carbon dioxide gas system. As a result, the present invention can be utilized more satisfactorily. Furthermore, it is because the supplied gas in the carbon dioxide gas system may be a gas that can be recycled as a raw material gas including ethylene, molecular oxygen, and a chlorine compound.

As such, the supplied gas in the carbon dioxide gas-based system is preferably a gas including water and a chlorine compound, and at this time, a non-absorbed gas in the carbon dioxide gas system is more preferably a gas including ethylene, molecular oxygen, and a chlorine compound. It is because in this case, the present invention can be applied not only to the heat exchanger in the reaction system but also to the heat exchanger in the carbon dioxide gas system and the present invention can be utilized more satisfactorily. Furthermore, it is because the reuse rate for the raw material gas is further increased, and more efficient production is enabled. Also, it is because a raw material gas in the reaction system that will be described below and a reaction product gas produced from the raw material gas, or a supplied gas and an unabsorbed gas in the carbon dioxide gas system that will be described below undergo heat exchange, and the heat energy produced by various reactions in the process can be recovered and utilized more effectively.

It is essential for the method for producing ethylene oxide according to an embodiment of the present invention that in regard to the heat exchanger, a gas to be cooled including water and a chlorine compound is cooled at a linear gas velocity on the heat exchanger inner tube side of 7 m/s or higher.

When the linear gas velocity on the heat exchanger inner tube side is less than 7 m/s, at the time of long-term production, the frequency of occurrence of corrosion in heat exchanger inner tubes, particularly corrosion called pitting corrosion when heat exchanger inner tubes made of stainless steel, is markedly increased. In a case in which a heat exchanger is corroded, the heat exchanger cannot be used, and ethylene oxide cannot be produced. Here, pitting corrosion refers to a phenomenon in which a passive state film of stainless steel is partially destroyed, an electrochemical reaction occurs at that part, and thereby stainless steel is corroded in a point form or in a pit form. As described above, in a case in which the raw material gas includes a chlorine compound, when the gas to be cooled that is cooled by the heat exchanger includes a chlorine compound and water, corrosion of stainless steel occurs; however, a chlorine compound in a gas state, for example, an organic chlorine compound itself, which is included in the raw material gas, does not corrode stainless steel. From this, the inventors of the present invention consider that the occurrence of corrosion in the heat exchanger inner tubes is caused by a factor that during long-term production, a chlorine compound is decomposed and is changed to a compound that is capable of destroying a passive film, such as hydrochloric acid, and a factor that such a compound partially adheres to inner tubes and is retained inside the heat exchanger inner tubes. Furthermore, since corrosion of stainless steel occurs on the heat exchanger inner tube side, which is the side that is cooled in the heat exchanger, although the details are not clearly understood, when the gas temperature is lowered inside the heat exchanger, the component that condenses on the heat exchanger inner tube side accelerates decomposition or retention of the chlorine compound. Here, since corrosion of the heat exchanger inner tubes is suppressed by setting the linear gas velocity on the heat exchanger inner tube side to 7 m/s or higher, it is speculated that a certain effect of suppressing decomposition of a chlorine compound, retention of the chlorine compound, or retention of a compound causative of corrosion, such as flicking off and removing a chlorine compound that can be changed to a compound causing corrosion, or a component that accelerates retention of the chlorine compound can be realized by setting the linear gas velocity equal to or higher than a certain value.

Here, the linear gas velocity on the heat exchanger inner tube side is preferably from 7 m/s to 30 m/s. The reason for this is that the upper limit of the linear gas velocity on the heat exchanger inner tube side is not particularly limited; however, it is necessary to set the linear gas velocity to a velocity at which the heat exchanger inner tubes are not damaged. It is also because, although the linear gas velocity may vary depending on the type and configuration of the heat exchanger, it is preferable to set the linear gas velocity on the side of general heat exchanger inner tubes to a value equal to or less than this value. From such a viewpoint, the linear gas velocity on the heat exchanger inner tube side is more preferably from 7 m/s to 25 m/s, even more preferably from 8 m/s to 20 m/s, and particularly preferably from 9 m/s to 15 m/s. Meanwhile, the linear gas velocity on the heat exchanger inner tube side can be controlled by the speed of rotation of a boosting blower for the raw material gas.

The heat exchanger for cooling the gas to be cooled including water and a chlorine compound is such that the temperature at the inlet of the heat exchanger inner tubes is higher than or equal to the dew point of water, and it is preferable that the gas to be cooled including water and a chlorine compound is cooled so that the temperature at the outlet of the heat exchanger inner tubes becomes lower than or equal to the dew point of water. In such a heat exchanger, when the gas on the heat exchanger inner tube side is cooled, the water vapor included in the gas is condensed, and thus, drainage of liquid water occurs. Drainage represents liquid water that adheres to the heat exchanger inner tubes after being produced when latent heat in the thermal energy possessed by water vapor is transferred from water vapor to the heat-absorbing medium of the heat exchanger, consequently the temperature becomes a temperature lower than or equal to the dew point, and steam is condensed. Here, the reason why the effects of the present invention are exhibited more noticeably in a heat exchanger where drainage occurs is that when the chlorine compound dissolves in the drainage, retention of the chlorine compound on the heat exchanger inner tube side is more likely to occur, and thus, decomposition of the chlorine compound is also further accelerated. Furthermore, it is speculated to be because when the difference between the temperature at the inlet of the heat exchanger inner tubes and the temperature at the outlet of the heat exchanger inner tubes is large, the amount of generation of drainage generally becomes large, and therefore, corrosion on the heat exchanger inner tube side is more likely to occur. The present invention can suppress corrosion without depending on the amount of generation of drainage, by cooling the gas to be cooled including water and a chlorine compound in a heat exchanger, at a linear gas velocity on the heat exchanger inner tube side of 7 m/s or higher. Therefore, it is more preferable that the present invention is used for a heat exchanger under the conditions in which the amount of generation of drainage is large, from the viewpoint of more effectively utilizing the corrosion prevention effect of the present invention. In addition, steam that causes drainage may be, for example, the water included in the raw material gas or the water produced by side reactions at the time of ethylene oxide production.

From this, it is preferable that the temperature at the heat exchanger inlet of the gas to be cooled including water and a chlorine compound is higher than or equal to the dew point of water, and the temperature is more preferably 100° C. or higher. Furthermore, the temperature at the heat exchanger inlet of the gas to be cooled including water and a chlorine compound is preferably 300° C. or lower, and more preferably 250° C. or lower. Meanwhile, the temperature at the heat exchanger outlet of the gas to be cooled including water and a chlorine compound is preferably 15° C. or higher. The temperature at the heat exchanger outlet of the gas to be cooled including water and a chlorine compound is preferably lower than or equal to the dew point of water, more preferably lower than the dew point of water, even more preferably 60° C. or lower, and particularly preferably 20° C. or lower.

Meanwhile, corrosion of the heat exchanger inner tubes can be checked by an examination by visual inspection, a fiberscope examination, and an eddy current testing. Regarding the evaluation method for the corrosion of heat exchanger inner tubes using these examinations, the details will be described in the Examples.

In the following description, specific embodiments for carrying out the present invention will be described in detail with reference to the drawings; however, the technical scope of the present invention should be defined based on the description of the claims and is not intended to be limited to the following embodiments only.

<<Reaction System>>

Figure 1:
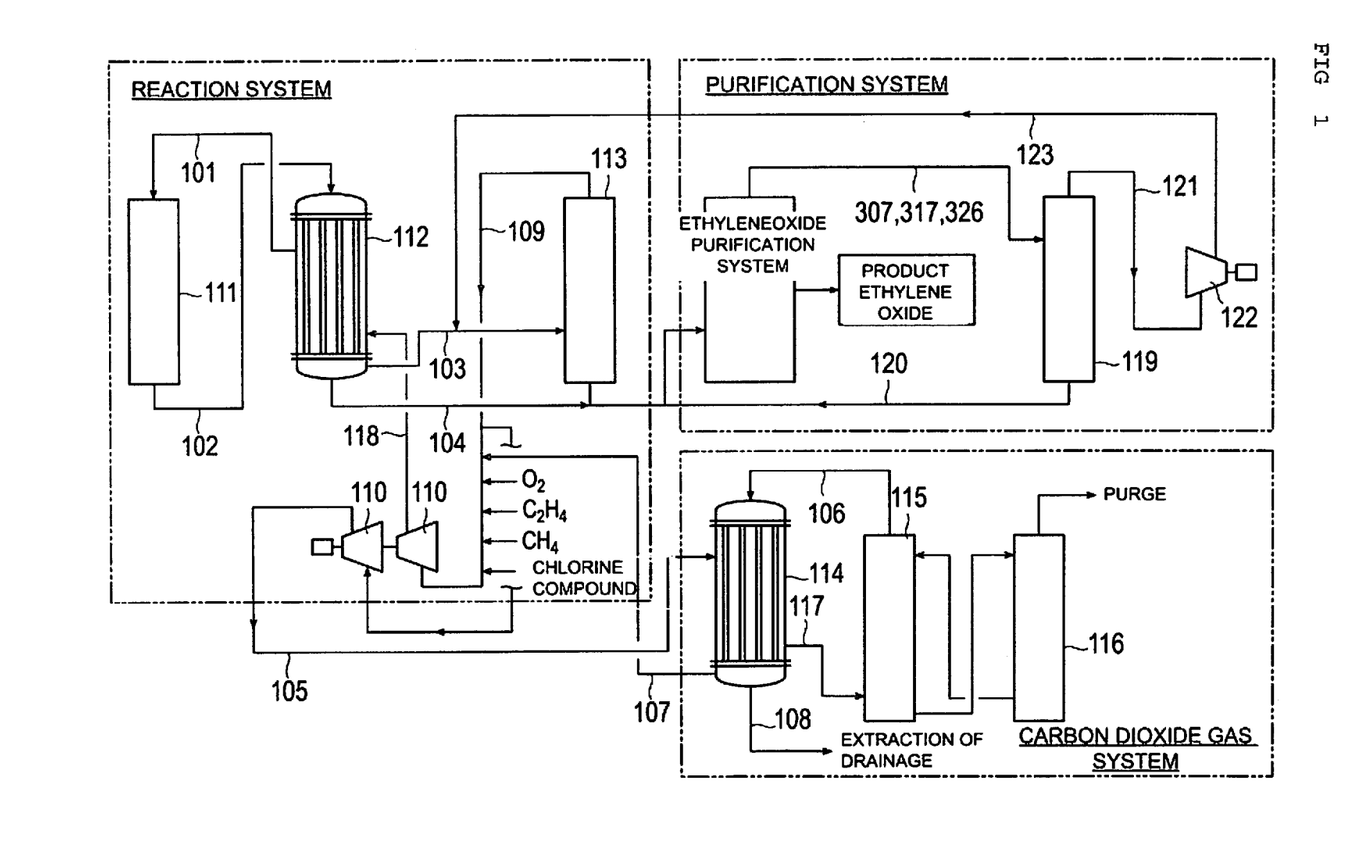
FIG. 1 is a block diagram illustrating a configuration example of a process for producing ethylene oxide, in which a method for producing ethylene oxide according to an embodiment of the present invention is carried out.

First, a system for producing ethylene oxide by an oxidation reaction of ethylene (also simply referred to as "reaction system") will be explained with reference to FIG. 1. FIG. 1 is a block diagram illustrating a configuration example of a process for producing ethylene oxide, in which a method for producing ethylene oxide according to an embodiment of the present invention is carried out. The process for producing ethylene oxide illustrated in FIG. 1 is composed of roughly divided three systems, namely, a reaction system, a carbon dioxide gas system, and a purification system.

The "reaction product gas containing ethylene oxide" used in the present invention may be any gas produced by a step of subjecting ethylene to catalytic vapor phase oxidation using a molecular oxygen-containing gas in the presence of a silver catalyst (hereinafter, also referred to as "ethylene oxidation reaction step"). Here, the molecular oxygen-containing gas is a gas containing molecular oxygen, and examples include air, pure oxygen, a mixture of pure oxygen and an inert gas, and an oxygen-enriched gas. This technology of catalytic vapor phase, oxidation reaction itself is widely known, and conventionally known findings can be referred to as appropriate in order to carry out the present invention. There are no particular limitations on the specific embodiment of the composition of the reaction product gas or the like; however, it is preferable that the reaction product gas includes 0.5% to 5% by mass of ethylene oxide and 0.3% to 1.2% by mass of generated water based on the mass of the reaction product gas, as well as 0.01 to 1,000 ppm by volume of a chlorine compound based on the volume of the reaction product gas. As an example, the reaction product gas may include 0.5% to 5% by mass of ethylene oxide based on the mass of the reaction product gas; 0.01 to 1,000 ppm by volume of a chlorine compound based on the volume of the reaction product gas; gases such unreacted oxygen, unreacted ethylene, generated water, carbon dioxide, nitrogen, argon, methane, and ethane; as well as trace amounts of aldehydes such as formaldehyde and acetaldehyde; and organic acids such as acetic acid.

According to FIG. 1, first, a raw material gas including ethylene, molecular oxygen, and a chlorine compound is boosted by a boosting blower 110, and then the gas is heated by passing the gas through a heat exchanger 112 through a conduit 118 and is supplied to an ethylene oxidation reactor 111 through a conduit 101. The ethylene oxidation reactor 111 is usually a multitubular reactor including a large number of reaction tubes packed with a silver catalyst. A reaction product gas produced in an ethylene oxidation reaction step is cooled by passing the gas through the heat exchanger 112 through a conduit 102 and then is supplied to an ethylene oxide absorption column (hereinafter, also simply referred to as "absorption column") 113 through a conduit 103. Specifically, the reaction product gas is supplied through the column bottom of the absorption column 313. Meanwhile, at the column top of the absorption column 113, an absorption liquid containing water as a main component is supplied. Counter flow contact between a gas and a liquid inside the absorption column 113 is thereby achieved, and ethylene oxide included in the reaction product gas (usually, 99% by mass or more is preferred) is absorbed by the absorption liquid. In addition to ethylene oxide, the chlorine compound, ethylene, oxygen, carbon dioxide, inert gases (nitrogen, argon, methane, ethane, and the like), point impurities such as formaldehyde produced in the ethylene oxidation reaction step, and high-boiling point impurities such as acetaldehyde and acetic acid are also simultaneously absorbed in substantial amounts. Meanwhile, the temperature of the reaction product gas supplied to the absorption column 113 is preferably about 15° C. to 80° C. There are no particular limitations on the composition of the absorption liquid, and in addition to the fact that water is included as a main component, propylene carbonate disclosed in JP 8-127573 A may also be used as an absorption liquid. Furthermore, if necessary, additives may be added to the absorption liquid. Examples of the additives that can be added to the absorption liquid include an antifoaming agent and a pH adjusting agent. Regarding the antifoaming agent, any antifoaming agent that is inert to ethylene oxide and byproduct ethylene glycol and has an antifoaming effect for the absorption liquid can be used, and as a representative example, a water-soluble silicon emulsion is effective because this emulsion exhibits excellent dispersibility in an absorption liquid, dilution stability, and thermal stability. Furthermore, regarding the pH adjusting agent, for example, a compound that can dissolve in the absorption liquid, such as hydroxide or carbonate of an alkali metal such as potassium or sodium, may be used and potassium hydroxide or sodium hydroxide is preferred. The pH of the absorption liquid is preferably 5 to 12, and more preferably 6 to 11.

Regarding the absorption column 113, usually a plate column type or packed column type absorption column can be used. Regarding the operation conditions for the absorption column 113, the ethylene oxide concentration in the reaction product gas is preferably 0.5% to 5% by mass, and more preferably 1.0% to 4% by mass, based on the mass of the reaction product gas, and the operation pressure of the absorption column 113 is preferably 0.2 to 4.0 MPa gauge, and more preferably 1.0 to 3.0 MPa gauge. The absorption operation is such that higher pressure is more advantageous; however, the employable value can be determined according to the operation pressure of the oxidation reactor. Furthermore, the molar flow rate ratio (L/V) of the absorption liquid with respect to the reaction product gas is usually preferably 0.30 to 2.00. The gas hourly space velocity in a standard state (GHSV [NTP]) of the reaction product gas is usually preferably 400 to 4,000 $h^{-1}$.

A gas including the chlorine-based compound, ethylene, oxygen, carbon dioxide, inert gases (nitrogen, argon, methane, and ethane), aldehyde, acidic substances, and the like, which were not absorbed in the absorption column 113, is discharged from the column top of the absorption column 113 through a conduit 109. After the pressure of this exhaust gas is increased by the boosting blower 110, the exhaust gas is heated by passing the exhaust gas through the heat exchanger 112 through the conduit 118 and is circulated to the ethylene oxidation reactor 111 through the conduit 101. Meanwhile, the details of the ethylene oxidation reaction step are as described above. Here, the ethylene oxidation reaction step is usually carried out in an oxidation reactor equipped with a large number of reaction tubes packed with a silver catalyst under pressurized conditions (a pressure of about 1.0 to 3.0 MPa gauge is preferred). Therefore, before the exhaust gas from the column top of the absorption column 113 is circulated into the ethylene oxidation reaction step, it is necessary to increase the pressure using pressure-increasing means such as the boosting blower 110.

The drainage generated in the heat exchanger 112 is taken out through the bottom of the heat exchanger 112 and is supplied to a conduit 202 (FIG. 1) through a conduit 104. The drainage joins with the column bottom liquid (absorption liquid) of the absorption column 113, and the mixed liquid supplied to a heat exchanger 203 through a conduit 202.

<<Carbon Dioxide Gas System>>

According to a preferred embodiment, as illustrated in FIG. 1, at least a portion of the gas discharged from the column top of the absorption column 113 is subjected to pressure increase by means of pressure-increasing means such as the boosting blower 110, heated by passing the gas through a heat exchanger 114 through a conduit 105, and supplied to a carbon dioxide gas absorption column 115 through a conduit 117. In the following description, a carbon dioxide gas recovery system (also simply referred to as "carbon dioxide gas system") that begins from the introduction of a gas into the carbon dioxide gas absorption column 115 will be explained with reference to FIG. 1.

As described above, in a case in which the gas discharged from the column top of the absorption column 113 is pressurized and introduced into the carbon dioxide gas absorption column 115, the gas pressure at that time is regulated to a certain pressure, preferably about 0.2 to 4.0 MPa gauge, and the gas temperature is regulated to a certain temperature, preferably about 80° C. to 120° C. In the subsequent stage of the carbon dioxide gas absorption column 115, a carbon dioxide gas stripper column 116 is installed, and at the column bottom of this carbon dioxide gas stripper column 116, an alkaline absorption liquid is supplied to the upper part of the carbon dioxide gas absorption column 115. Then, as a result of counter flow contact with this alkaline absorption liquid, the carbon dioxide gas, chlorine compound, ethylene, and oxygen, or small amounts of inert gases (for example, methane, ethane, nitrogen, argon, and the like) included in the gas introduced into the carbon dioxide gas absorption column 115 are absorbed. Unabsorbed gas that is discharged from the column top of the carbon dioxide gas absorption column 115 is cooled by passing the gas through the heat exchanger 114 through a conduit 106 and is circulated to a conduit 109 through a conduit 107 to be mixed with a chlorine compound, oxygen, ethylene, methane, and the like, which are replenished. Subsequently, the mixed gas is heated by passing the gas through the heat exchanger 112 and is circulated into the ethylene oxidation reactor 111.

Furthermore, the drainage generated inside the heat exchanger 114 is taken out from the bottom of the heat exchanger 114 and is discharged out of the system through a conduit 108.

The carbon dioxide gas-rich absorption liquid that has absorbed carbon dioxide gas in the carbon dioxide gas absorption column 115 is drawn out from the column bottom of the carbon dioxide gas absorption column and then is regulated to a certain pressure, preferably a pressure of about 0.01 to 0.5 MPa gauge, and a certain temperature, preferably a temperature of about 80° C. to 120° C. The regulated gas is supplied to the upper part of the carbon dioxide gas stripper column 116 having a reboiler (not shown in the diagram) at the column bottom. The absorption liquid undergoes a pressure flash at the liquid feeding part in the upper part of the carbon dioxide gas stripper column 116 due to the pressure difference between the carbon dioxide gas absorption column 115 and the carbon dioxide gas stripper column 116. Thereby, the carbon dioxide gas (preferably 10% to 30% by volume) and most of the inert gases in the absorption liquid are separated from the absorption liquid and discharged from the column top of the carbon dioxide gas stripper column 116.

The remaining carbon dioxide gas absorption liquid, from which a portion of carbon dioxide gas has been separated by the pressure flash described above, enters a gas-liquid contact part (not shown in the diagram) provided below the liquid feeding part and is subjected to counter flow contact with a gas mainly including the vapor produced in the reboiler (not shown in the diagram) and the carbon dioxide gas produced in the gas-liquid contact part (not shown in the diagram) or the part below the gas-liquid contact part. A portion of the carbon dioxide gas and most of the other inert gases in the absorption liquid are separated from the absorption liquid. Through a series of these processes in the carbon dioxide gas system, a high-purity carbon dioxide gas is obtained from parts ranging from the uppermost part to the lower part of the gas-liquid contact part (not shown in the diagram), and preferably from the inside of the carbon dioxide gas stripper column 116 below the gets-liquid contact part corresponding to a number of theoretical plates of 1 or greater required for gas-liquid contact. That is, in the gas-liquid contact part (not shown in the diagram), the inert gases in the carbon dioxide gas absorption liquid are subjected to counter flow gas-liquid contact with steam and a carbon dioxide gas including a trace amount of inert gases, which come up from the lower part, and the inert gases are stripped. As a result, the concentration of the inert gases is decreased to a very low level. Therefore, when the gas after this stripping is extracted, a high-purity carbon dioxide gas is obtained.

<<Purification System>>

Figure 2:
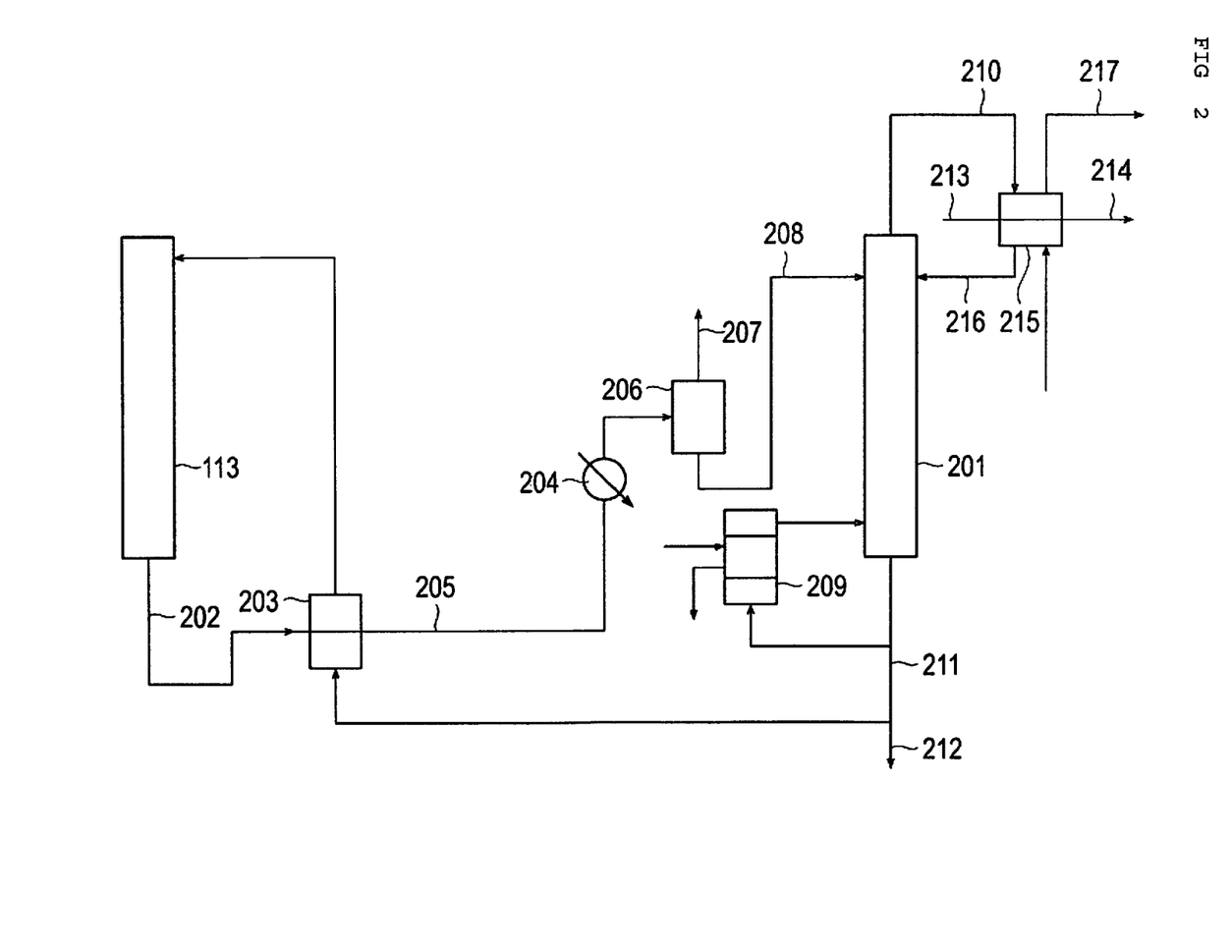
FIG. 2 is a block diagram illustrating a configuration example of a process for implementing a method for producing ethylene oxide according to the embodiment of the present invention.

The absorption liquid that has absorbed ethylene oxide in the absorption column 113 is sent to an ethylene oxide purification system (hereinafter, also simply referred to as "purification system") as a column bottom liquid of the absorption column 113. There are no particular limitations on the specific embodiment of the purification system, and conventionally known knowledge can be referred to as appropriate. For instance, the purification system usually includes a stripping step, a purification step, a dehydration step, a light fraction separation step, a heavy fraction separation step, and the like. In the following description, a purification system including some of these steps will be described with reference to FIG. 2 and FIG. 3. FIG. 2 is a block diagram illustrating a configuration example of a process for performing the process for producing ethylene oxide according to an embodiment of the present invention.

The column bottom liquid (absorption liquid) of the absorption column 113 is usually heated in advance, before being supplied to the ethylene oxide stripper column (hereinafter, also simply referred to as "stripper column") 201, to a temperature appropriate for stripping at the stripper column 201. Specifically, as illustrated in FIG. 2, the column bottom liquid (absorption liquid) of the absorption column 113 is supplied to the heat exchanger 203 through the conduit 202. Then, in this heat exchanger 203, heat exchange occurs between this column bottom liquid and the column bottom liquid of the stripper column 201, and if necessary, the column bottom liquid heated by a heater 204. Thus, the column bottom liquid (absorption liquid) of the absorption column 113 is heated to a certain temperature, preferably to a temperature of about 70° C. to 110° C. According to the present embodiment, the column bottom liquid (absorption liquid) of the absorption column 113, which has been heated by the heat exchange with the column bottom liquid of the stripper column 201, is supplied to a gas-liquid separation tank 206 through a conduit 205. In the gas-liquid separation tank 206, a light fraction gas of inert gases including a portion of ethylene oxide and water is separated and is discharged through a conduit 207. On the other hand, the remaining absorption liquid from which the light fraction gas has been flashed is supplied to the upper part of the stripper column 201 through a conduit 208. Meanwhile, particularly at a site where ethylene oxide and water coexist under high temperature conditions as in the case of the conduit 208, the retention time for the absorption liquid can be shortened by making the distance of disposition of the site as short as possible, and as a result, prevention of production of ethylene glycol as a byproduct can be promoted.

Subsequently, for example, as illustrated in FIG. 2, a heating medium such as steam is supplied to a reboiler 209, and the stripper column 201 is heated by using the heating medium that has been heated by the reboiler 209, or the stripper column 201 is heated by directly supplying steam to the column bottom of the stripper column 201. When the stripper column 201 is heated as such, the ethylene oxide (usually, 99% by mass or more thereof is preferred) included in the absorption liquid supplied from the upper part of the stripper column 201 is stripped and discharged from the column top of the stripper column 201 through a conduit 210. The operation conditions for the stripper column 201 are preferably such that the operating pressure (column top pressure) is 3 to 60 kPa gauge, and more preferably 3 to 30 kPa gauge. As the column top pressure is lower, the temperature inside the column is decreased, and consequently, production of ethylene glycol as a byproduct from ethylene oxide in the column tends to be suppressed. However, since ethylene oxide is a substance that is relatively easily ignitable, from the viewpoint of preventing leak-in of oxygen into the system, operation at a pressure lower than or equal to the atmospheric pressure is usually not implemented, and the column is operated at a pressure slightly higher than the atmospheric pressure as described above. Regarding the temperature conditions for the stripper column 201, the column top temperature is preferably 82° C. to 93° C., and the column bottom temperature is preferably 101° C. to 115° C.

The remaining absorption liquid obtainable after stripping of ethylene oxide is extracted as a column bottom liquid of the stripper column 201 as illustrated in FIG. 2 and is supplied to the upper part of the absorption column 113 as an absorption liquid for the absorption column 113. Thus, the absorption liquid can be used in circulation. However, for the purpose of regulating the composition of the absorption liquid, fresh water or, if necessary, the above-mentioned additives may be supplied to the absorption column 113 through a conduit that is separately provided. Furthermore, it is preferable to maintain the ethylene glycol concentration in the absorption liquid that is supplied to the absorption column 113 at a constant level. For this reason, a portion of the absorption liquid that is circulated between the absorption column 113 and the stripper column 201 is extracted from the column bottom of the stripper column 201. Here, the column bottom liquid of the stripper column 201 does not substantially include ethylene oxide. Specifically, the concentration of ethylene oxide included in the column bottom liquid is preferably 10 ppm by mass or less, and more preferably 0.5 ppm by mass or less. This column bottom liquid contains ethylene glycol produced as a byproduct in the absorption liquid between the ethylene oxidation reaction step and the ethylene oxide stripping step, and a portion thereof is extracted through a conduit 211 and a conduit 212. The extracted liquid is submitted to a combustion treatment or is supplied to an ethylene glycol concentration step for concentrating in order to collect ethylene glycol included therein. Furthermore, depending on cases, the ethylene glycol included in the extracted liquid can be collected directly, or after being subjected to the ethylene glycol concentration step, the ethylene glycol can be recovered as a fiber grade product, by subjecting the ethylene glycol to the chemical treatments disclosed in JP 45-9926 B, JP 04-28247 B, and the like as well as physical treatments as necessary.

Since the column bottom liquid of the stripper column 201 includes low-boiling point impurities such as formaldehyde, and high-boiling point impurities such as acetaldehyde and acetic acid, when a portion thereof is extracted out of the system as described above, there is also an advantage that accumulation of these impurities in the absorption liquid that is circulated to the absorption column 113 can be prevented.

The stripped material including ethylene oxide, which has been stripped from the column top of the stripper column 201, is sent through the conduit 210 to a stripper column condenser 215 where cooling water passes through a conduit 213 and a conduit 214. A condensed liquid is refluxed to the column top of the stripper column 201 through a conduit 216, and uncondensed vapor is supplied to a dehydration column 301 (FIG. 3) through a conduit 217.

The vapor including ethylene oxide, which has been supplied to the dehydration column 301, is brought into contact with the liquid to be refluxed through a conduit 302 and becomes a vapor with a higher concentration of ethylene oxide. A liquid extracted from the column bottom and having a lower ethylene oxide concentration is sent to the stripper column condenser 215 (FIG. 2) through a conduit.

The vapor including ethylene oxide, which has been discharged from the column top of the dehydration column 301, is sent through a conduit 303 to a dehydration column condenser 306 where cooling water passes through a conduit 304 and a conduit 305. A portion of the condensed liquid is refluxed to the column top of the dehydration column 301 through the conduit 302, and uncondensed vapor (ethylene oxide-containing uncondensed gas) of the dehydration column condenser 306 is supplied to an ethylene oxide reabsorption column (hereinafter, also simply referred to as "reabsorption column") 119 illustrated in FIG. 1 through a conduit 307.

The remaining portion of the condensed liquid of the dehydration column condenser 306 is supplied to a light fraction separation column 309 through a conduit 308. The condensed liquid is heated by a method of heating by means of a reboiler 310 of the light fraction separation column 309 through a conduit 311 with a heating medium such as steam. The ethylene oxide vapor including a light fraction from the column top of the light fraction separation column 309 is sent through a conduit 312 to a light fraction separation column condenser 315 where cooling water passes through a conduit 313 and a conduit 314, and a condensed liquid is refluxed to the column top of the light fraction separation column 309 through a conduit 316. Uncondensed vapor of the light fraction separation column condenser 315 (ethylene oxide-containing uncondensed gas) is supplied through a conduit 317 to the reabsorption column 119 illustrated in FIG. 1 for the recovery of ethylene oxide.

The column bottom liquid of the light fraction separation column 309 is supplied to an ethylene oxide purification column (hereinafter, also simply referred to as "purification column") 319 through a conduit 318. Steam having a certain pressure, preferably a pressure of about 0.05 to 0.10 MPa gauge, is supplied to a reboiler 320 of the purification column 319, and purification is performed, preferably at a column bottom temperature of the purification column 319 of 35° C. to 80° C. and a column bottom pressure of the purification column 319 of 0.10 to 0.80 MPa gauge. From the column top of the purification column 319, ethylene oxide vapor preferably at a column top temperature of 35° C. to 75° C. and a column top pressure of 0.10 to 0.80 MPa gauge is sent to a purification column condenser 323 where cooling water passes through a conduit 321 and a conduit 322, and ethylene oxide is liquefied. A portion thereof is supplied as a reflux liquid to the column top of the purification column 319 through a conduit 324, and the remaining portion is extracted as product ethylene oxide (product EO) through a conduit 325. Uncondensed vapor of the purification column condenser 323 (ethylene oxide-containing uncondensed gas) is supplied to the reabsorption column 119 illustrated in FIG. 1 through a conduit 326 for the recovery of ethylene oxide.

The column bottom liquid of the purification column 319 is extracted, if necessary, through a conduit 327 for the purpose of separation of a heavy fraction of high-boiling point impurities such as acetaldehyde water, and acetic acid.

As described above, uncondensed vapor discharged from the purification system (in the embodiment illustrated in FIG. 3, uncondensed vapor coming from the dehydration column condenser 306, light fraction separation column condenser 315, and purification column condenser 323) includes ethylene oxide. Accordingly, such uncondensed vapor is supplied to the reabsorption column 119 illustrated in FIG. 1.

In the reabsorption column 119, similarly to the absorption column 113 described above, ethylene oxide is reabsorbed by counter flow contact with an absorption liquid. Here, in regard to the composition or pH of the absorption liquid used for reabsorption of ethylene oxide in the reabsorption column 119, the form of the reabsorption column (plate column type or packed column type), and the like, since the details are similar to the matters described above in connection with the absorption column 113, no further detailed explanation will be provided here. The operating pressure of the reabsorption column 119 is preferably 100 to 150 kPa gauge.

The column bottom liquid of the reabsorption column 119 is circulated to the purification system (in the present embodiment, specifically stripper column 201) through a conduit 120, similarly to the column bottom liquid of the absorption column 113 described above. More particularly, the column bottom liquid of the reabsorption column 119 is circulated to the conduit 202 illustrated in FIG. 2 and is heated in advance, and then the heated column bottom liquid is introduced into the stripper column 201.

Meanwhile, the uncondensed gas that was not absorbed in the reabsorption column 119 is discharged from the column top of the reabsorption column 119 through a conduit 121. According to an embodiment, the uncondensed gas discharged through the conduit 121 is subjected to pressure increase by a gas compressor 122 and then is circulated to the absorption column 113 via a conduit 123 and a conduit 103. However, since the uncondensed gas discharged from the column top of the reabsorption column 119 includes a large amount (usually about 5% to 60% by volume) of a carbon dioxide gas, when this uncondensed gas is circulated to the absorption column 113, the amount of a carbon dioxide gas in the gas supplied from the absorption column 113 to the carbon dioxide gas absorption column 115 is increased. Then, the amount of the carbon dioxide gas to be treated at the carbon dioxide gas absorption column 115 and the carbon dioxide gas stripper column 116 is increased, and there is a possibility that it may become necessary to increase the amount of vapor to be introduced into the reboiler (not shown in the diagram) of the carbon dioxide gas stripper column 116, or it may become necessary to increase the amount of introduction of a carbon dioxide gas absorption promoter. Therefore, the uncondensed gas discharged from the column top of the reabsorption column 119 through the conduit 121 may be supplied to the carbon dioxide gas absorption column 115 after the pressure is increased by the gas compressor 122. By employing such a configuration, the flow rate of the gas supplied to the carbon dioxide gas absorption column 115 is increased only slightly; however, the uncondensed gas discharged from the column top of the ethylene oxide reabsorption column as described above includes a large amount (usually, about 5% to 60% by volume) of a carbon dioxide gas. Therefore, when the ethylene oxide-containing uncondensed gas discharged from the column top of the reabsorption column 119 is supplied to the carbon dioxide gas absorption column 115, the carbon dioxide gas concentration in the gas supplied to the carbon dioxide gas absorption column 115 increases only slightly. As such, according to the present embodiment, various industrially advantageous effects can be provided by introducing a gas including a higher concentration of a carbon dioxide gas into the carbon dioxide gas system.

In addition, it is preferable that the suction pressure of the gas compressor 122 for increasing the pressure of the uncondensed gas discharged from the column top of the reabsorption column 119 through the conduit 121, is a slightly increased pressure. Specifically, the suction pressure is preferably 3 to 5 kPa gauge. By employing such a configuration, oxygen inflow from the atmosphere into the gas compressor 122 can be prevented, and the risk of explosion caused by compressing a mixed gas of oxygen and a combustible gas at the gas compressor 122 can be avoided.

Furthermore, although the uncondensed gas discharged from the column top of the reabsorption column 119 includes ethylene, which is a reaction raw material, since the unabsorbed gas discharged from the column top of the carbon dioxide gas absorption column 115 as described above passes through the conduit 109 and the conduit 118 and is heated bypassing the gas through the heat exchanger 112 and circulated to the ethylene oxidation reactor 111, and ethylene is hardly absorbed in the carbon dioxide gas absorption column 115, even if a configuration such as described above is employed, there is no risk of the occurrence of any loss of ethylene, which is a reaction raw material.

EXAMPLES

Hereinafter, the embodiments of the present invention will be described in more detail using Examples. However, the technical scope of the present invention is not intended to be limited to the following embodiments.

<Ethylene Oxide Production Process>

Example 1

Figure 3:
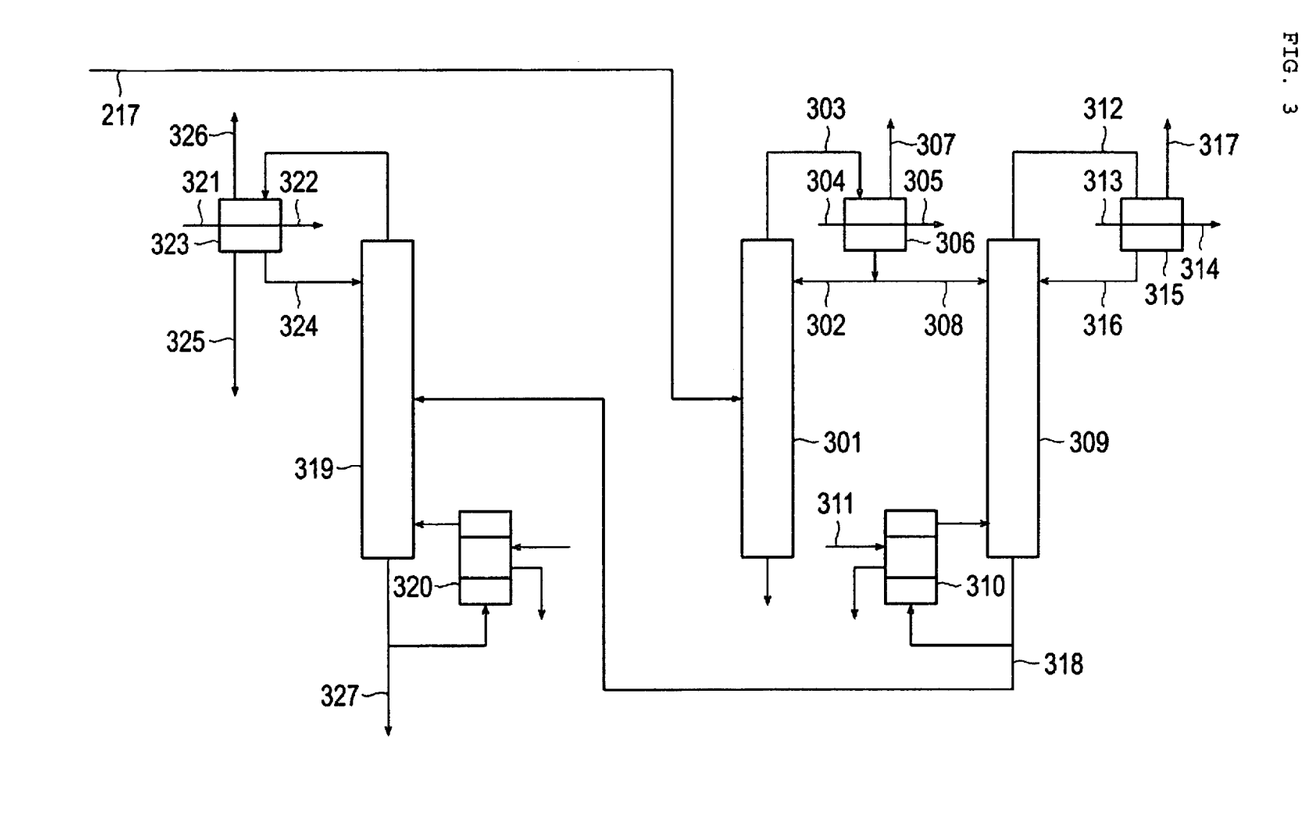
FIG. 3 is a block diagram illustrating a configuration example of a purification step that is carried out until stripped ethylene oxide is finally purified.

Ethylene oxide was produced by the process for producing ethylene oxide illustrated in FIG. 1 to FIG. 3. In the present experiment, as the production apparatus for performing the production process of FIG. 1 to FIG. 3, a pilot plant similar to the real plant was used, except that the tube diameters (tube cross-sectional areas) of the heat exchangers were different, and operation was performed at a gas composition and operation conditions to those of the real plant. Thus, ethylene oxide was produced.

Here, a raw material gas at the conduit 101 included 27% by mass of ethylene and 11% by mass of a molecular oxygen gas based on the mass of the raw material gas, and furthermore, chlorinated ethylene as a reaction adjusting agent was added to the raw material gas to a concentration of 6 ppm by volume based on the volume of the raw material gas.

At this time, as the heat exchanger 112 for the reaction system and the heat exchanger 114 for the carbon dioxide gas system, vertical heat exchangers in which the material for the inner tubes was stainless steel (SUS430: Cr content 16% to 18% by mass and Mo content 0% by mass) were used.

The speed of rotation of the boosting blower 110 for the raw material gas was adjusted so that the linear gas velocity on the inner tube side of the heat exchanger 112 and the heat exchanger 114 would be 10.4 m/s. Here, the linear gas velocity on the inner tube side of the heat exchanger 112 was calculated from the flow rate meter provided in the conduit 101, the proportions of the main reaction and the side reaction in the reactor 111, the ethylene conversion rate, and the temperature of the conduit 102. The linear gas velocity on the inner tube side of the heat exchanger 114 was calculated from the flow rate meter provided in the conduit 105, the proportions of the main reaction and the side reaction at the reactor 111, the ethylene conversion rate, the outlet temperature and outlet pressure of the carbon dioxide gas absorption column 115, and the proportion of absorbed carbon dioxide gas.

Meanwhile, the dew point of water at the gas composition and pressure in the conduit 102 was 67° C., and the dew point of water at the gas composition and pressure in the conduit 106 was 104° C.

Here, in regard to the ethylene oxide production process, the respective component amounts of carbon dioxide gas, ethylene oxide (EO), water, and a residual gas, which is composed of gases other than these components (the unit of the composition is "mass %"), at various positions during the process and the operation conditions are presented in Table 1.

Here, the residual gas included ethylene, molecular oxygen, and a chlorine compound, and the residual gas was inert at the positions for measuring the respective component amounts during the process.

In connection with the various component amounts (mass %), regarding the values for the carbon dioxide gas, ethylene oxide (EO), and the residual gas, values obtained by rounding off to two decimal places were used. Furthermore, regarding the value for water, values obtained by rounding off to three decimal places were used. The unit MPa gauge will be described as MPaG. In the following description, the same also applies to Table 2 and Table 3.

Example 2

Ethylene oxide was produced in the same manner as in Example 1, except that the outlet temperature of the heat exchanger employed in Example 1 was set to a higher temperature, and the operation conditions were changed to the conditions shown in Table 2.

The gas composition and the operation conditions are presented in Table 2.

Example 3

Ethylene oxide was produced the same manner as in Example 1, except that the outlet temperature of the heat exchanger employed in Example 1 was set to a lower temperature, and the operation conditions were changed to the conditions shown in Table 3.

The gas composition and the operation conditions are presented in Table 3.

Comparative Example 1

In Example 1, ethylene oxide was produced in the same manner as in Example 1, except that the speed of rotation of the boosting blower 110 for the raw material gas was adjusted such that the linear gas velocity on the inner tube sides of the heat exchanger 112 and the heat exchanger 114 would be 5 m/s. Here, even when the linear gas velocity was changed, there was no change in the gas composition and the amount of drainage (amount of water in the conduit 104 and the conduit 108), and the gas composition and the operation conditions were as shown in Table 1.

Comparative Example 2

In Example 2, ethylene oxide was produced in the same manner as in Example 2, except that the speed of rotation of the boosting blower 110 for the raw material gas was adjusted such that the linear gas velocity on the inner tube sides of the heat exchanger 112 and the heat exchanger 114 employed in Example 2 would be 5 m/s. Here, even when the linear gas velocity was changed, there was no change in the gas composition and the amount of drainage, and the gas composition and the operation conditions were as shown in Table 2.

Comparative Example 3

In Example 3, ethylene oxide was produced in the same manner as in Example 3, except that the speed of rotation of the boosting blower 110 for the raw material gas such that the linear gas velocity on the inner tube sides of the heat exchanger 112 and the heat exchanger 114 employed in Example 3 would be 5 m/s. Here, even when the linear gas velocity was changed, there was no change in the gas composition and the amount of drainage, and the gas composition and the operation conditions were as shown in Table 3.

TABLE 1

| | | Position of measurement | | | | | | | |
| --- | --- | --- | --- | --- | --- | --- | --- | --- | --- |
| | | 101 | 102 | 103 | 104 | 105 | 106 | 107 | 108 |
| Respective component amounts (mass %) | Residual gas | 88.8 | 82.4 | 82.4 | 0 | 86.3 | 96.1 | 98.9 | 0 |
| | Carbon dioxide gas | 11.1 | 12.9 | 12.9 | 0 | 13.5 | 0 | 0 | 0 |
| | Ethylene oxide | 0 | 3.9 | 3.9 | 0 | 0 | 0 | 0 | 0 |
| | Water | 0.12 | 0.84 | 0.76 | 100 | 0.16 | 3.93 | 1.11 | 100 |
| Flow rate (Kg/h) | | 317,652 | 317,652 | 317,401 | 2.51 | 43,007 | 38,661 | 37,556 | 1,105 |
| Pressure (MPaG) | | 2.50 | 2.35 | 2.33 | 2.33 | 2.35 | 2.30 | 2.28 | 2.28 |
| Temperature (° C.) | | 185 | 210 | 65 | 65 | 30 | 104 | 70 | 70 |
| State | | Gas | Gas | Gas | Liquid | Gas | Gas | Gas | Liquid |

TABLE 2

| | | Position of measurement | | | | | | | |
| --- | --- | --- | --- | --- | --- | --- | --- | --- | --- |
| | | 101 | 102 | 103 | 104 | 105 | 106 | 107 | 108 |
| Respective component amounts (mass %) | Residual gas | 88.8 | 82.4 | 82.4 | 0 | 86.3 | 96.1 | 98.3 | 0 |
| | Carbon dioxide gas | 11.1 | 12.9 | 12.9 | 0 | 13.5 | 0 | 0 | 0 |
| | Ethylene oxide | 0 | 3.9 | 3.9 | 0 | 0 | 0 | 0 | 0 |
| | Water | 0.12 | 0.84 | 0.84 | 100 | 0.16 | 3.93 | 1.66 | 100 |
| Flow rate (Kg/h) | | 317,652 | 317,652 | 317,651 | 1 | 43,007 | 38,661 | 37,768 | 893 |
| Pressure (MPaG) | | 2.50 | 2.35 | 2.33 | 2.33 | 2.35 | 2.30 | 2.28 | 2.28 |
| Temperature (° C.) | | 185 | 210 | 67 | 67 | 30 | 104 | 80 | 80 |
| State | | Gas | Gas | Gas | Liquid | Gas | Gas | Gas | Liquid |

TABLE 3

| | | Position of measurement | | | | | | | |
|---|---|---|---|---|---|---|---|---|---|
| | | 101 | 102 | 103 | 104 | 105 | 106 | 107 | 108 |
| Respective component amounts (mass %) | Residual gas | 88.8 | 82.4 | 82.6 | 0 | 86.3 | 96.1 | 99.3 | 0 |
| | Carbon dioxide gas | 11.1 | 12.9 | 12.9 | 0 | 13.5 | 0 | 0 | 0 |
| | Ethylene oxide | 0 | 3.9 | 3.9 | 0 | 0 | 0 | 0 | 0 |
| | Water | 0.12 | 0.84 | 0.62 | 100 | 0.16 | 3.93 | 0.71 | 100 |
| Flow rate (Kg/h) | | 317,652 | 317,652 | 316,924 | 728 | 43,007 | 38,661 | 37,403 | 1258 |
| Pressure (MPaG) | | 2.50 | 2.35 | 2.33 | 2.33 | 2.35 | 2.30 | 2.28 | 2.28 |
| Temperature (° C.) | | 185 | 210 | 60 | 60 | 30 | 104 | 60 | 60 |
| State | | Gas | Gas | Gas | Liquid | Gas | Gas | Gas | Liquid |

In all of Examples 1 to 3 and Comparative Examples 1 to 3, the gas in the conduit 105 included 25% by mass of ethylene and 8% by mass of molecular oxygen on a mass basis, and 6 ppm by volume of a chlorine compound on a volume basis.

The gas in the conduit 102 included 6 ppm by volume of a chlorine compound on a volume basis, and the gas in the conduit 106 included 5 ppm by volume of a chlorine compound on a volume basis.

<Evaluation of Corrosion in Heat Exchanger Inner Tubes>

Unless particularly stated otherwise, the operation of an evaluation of corrosion in heat exchanger inner tubes is carried out under the conditions of room temperature (20° C. to 25° C.)/relative humidity of 40% RH to 50% RH.

In the pilot plant, production was carried out for one year under the conditions of Examples 1 to 3 and Comparative Examples 1 to 3, and then the following examination by visual inspection, fiberscope examination, and eddy current testing of the inner tubes of the heat exchanger 112 and the heat exchanger 114 were carried out. These evaluations were performed every time after production of ethylene oxide had been carried out for one year, by temporarily stopping the production. Then, after completion of the evaluations, production of ethylene oxide was resumed. Here, regarding the inner tubes of the heat exchanger 112 and the heat exchanger 114, the same ones were used continuously from the initiation of production.

(Examination by Visual Inspection)

The inner tubes of the heat exchanger 112 and the heat exchanger 114 used for the production of ethylene oxide respectively under the conditions of Examples 1 to 3 and Comparative Examples 1 to 3 were respectively checked by visual inspection, and the presence or absence of corrosion and shape change were checked. The following evaluation criteria were employed.

◯: No corrosion x: Corrosion occurred (Fiberscope Examination)

A fiberscope camera (IPLEX®) MX R series manufactured by Olympus Corporation) was inserted into the inner tubes of the heat exchanger 112 and the heat exchanger 114 used for the production of ethylene oxide respectively under the conditions of Examples 1 to 3 and Comparative Examples 1 to 3, and the image was checked by visual inspection. Thereby, the presence or absence of corrosion and shape change in the inner tubes were checked. The following evaluation criteria were employed.

◯: No corrosion x: Corrosion occurred (Eddy Current Testing)

An eddy current testing is a kind of electromagnetic testing and is an examination of evaluating the presence or absence of defects in a test specimen, changes in the shape and dimension, the composition, and the like, by using the fact that when a magnetic field that changes over time by a coil through which an alternating current is passed is applied to a test specimen, an eddy current produced in the test specimen changes defects in the test specimen, shape, dimension, electrical conductivity, and the like. More specifically, in an eddy current testing, a test specimen is scanned with a probe having two coils for examination incorporated therein, and any changes in the eddy current produced at defect portions are investigated. Here, the two coils are bridged to four sides, and examination is performed by checking the presence or absence of defects in the test specimen and any thickness change in the test specimen by inducing a change in the impedance of the coils to be examined caused by a change in the eddy current. Meanwhile, since the eddy current testing is a non-destructive test to materials, the examination is suitable for checking changes over time in a member during a production process at a fixed interval of a certain time.

In the present experiment, the thickness change (ratio (%) of a reduced thickness (reduced thickness) with respect to the initial thickness) in various heat exchanger inner tubes was evaluated by examining the interior of the inner tubes of the heat exchanger 112 and the heat exchanger 114 used for the production of ethylene oxide respectively under the conditions of Examples 1 to 3 and Comparative Examples 1 to 3 by an eddy current testing. Here, regarding the eddy current tester, flaw detector: ND-382D by NDK Co., Ltd. and recorder: RA2300 by A&D Co., Ltd. were used, and measurement was performed by differential method: 38 kHz and absolute method: 38 kHz.

In regard to the inner tubes of the heat exchanger 112 and the heat exchanger 114, the evaluation results for the examination by visual inspection, fiberscope examination, and eddy current testing are described below. Here, the evaluation results obtained after a lapse of one year from the initiation of ethylene oxide production are presented in Table 4, and the evaluation results obtained after a lapse of two years from the initiation of ethylene oxide production are presented in Table 5.

TABLE 4

(Evaluation results obtained after lapse of one year from initiation of ethylene oxide production)

| | Heat exchanger 112 | | | Heat exchanger 114 | | |
|---|---|---|---|---|---|---|
| | Visual inspection Presence or absence of corrosion | Fiberscope examination Presence or absence of corrosion | Eddy current testing Ratio of reduced thickness (%) | Visual inspection Presence or absence of corrosion | Fiberscope examination Presence or absence of corrosion | Eddy current testing Ratio of reduced thickness (%) |
| Example 1 | ○ | ○ | 0 | ○ | ○ | 0 |
| Example 2 | ○ | ○ | 0 | ○ | ○ | 0 |
| Example 3 | ○ | ○ | 0 | ○ | ○ | 0 |
| Comparative Example 1 | X | X | 0 | X | X | 0 |
| Comparative Example 2 | X | X | 0 | X | X | 0 |
| Comparative Example 3 | X | X | 0 | X | X | 0 |

TABLE 5

(Evaluation results obtained after lapse of two years from initiation of ethylene oxide production)

| | Heat exchanger 112 | | | Heat exchanger 114 | | |
|---|---|---|---|---|---|---|
| | Visual inspection Presence or absence of corrosion | Fiberscope examination Presence or absence of corrosion | Eddy current testing Ratio of reduced thickness (%) | Visual inspection Presence or absence of corrosion | Fiberscope examination Presence or absence of corrosion | Eddy current testing Ratio of reduced thickness (%) |
| Example 1 | ○ | ○ | 0 | ○ | ○ | 0 |
| Example 2 | ○ | ○ | 0 | ○ | ○ | 0 |
| Example 3 | ○ | ○ | 0 | ○ | ○ | 0 |
| Comparative Example 1 | X | X | 10 | X | X | 5 |
| Comparative Example 2 | X | X | 5 | X | X | 4 |
| Comparative Example 3 | X | X | 29 | X | X | 6 |

As is obvious from the results shown in Table 4 and Table 5, it was confirmed from a comparison between Examples and Comparative Examples that when a gas to be cooled including water and a chlorine compound is cooled with a heat exchanger, corrosion of heat exchanger inner tubes is markedly suppressed by adjusting the linear gas velocity of the gas to be cooled including water and a chlorine compound on the heat exchanger inner tube side, 7 m/s or higher.

As in the cases of Examples 1 to 3 and Comparative Examples 1 to 3, it was confirmed that even when the temperature on the heat exchanger outlet side is changed, corrosion of heat exchanger inner tubes is markedly suppressed by employing a high linear gas velocity as specified in the present invention. These results show that an excellent corrosion prevention effect is obtained, irrespective of the size of the amount of drainage produced inside a heat exchanger, by employing a high linear gas velocity as specified in the present invention.

As described above, the process for producing ethylene oxide according to the present invention can markedly decrease the frequency of replacement of heat exchangers, and therefore, an industrially very advantageous effect that the production efficiency can be increased is provided.

The present patent application is based on Japanese Patent Application No. 2016-069720 filed on Mar. 30, 2016, the entire disclosure of which is incorporated herein by reference.

REFERENCE SIGNS LIST 101, 102, 103, 104, 105, 106, 107, 108, 109, 117, 118, 120, 121, 123 Conduit
110 Boosting blower
111 Ethylene oxidation reactor
112 Heat exchanger
113 Ethylene oxide absorption column
114 Heat exchanger
115 Carbon dioxide gas absorption column
116 Carbon dioxide gas stripper column
119 Ethylene oxide reabsorption column
122 Gas compressor
201 Ethylene oxide stripper column
202, 205, 207, 208, 210, 211, 212, 213, 214, 216, 217 Conduit
203 Heat exchanger
204 Heater
206 Gas-liquid separation tank
209 Stripper column reboiler
215 Stripper column condenser
301 Dehydration column
302, 303, 304, 305, 307, 308, 311, 312, 313, 314, 316, 317, 318, 321, 322, 324, 325, 326, 327 Conduit
306 Dehydration column condenser
309 Light fraction separation column
310 Light fraction separation column reboiler
315 Light fraction separation column condenser 319 Ethylene oxide purification column
320 Purification column reboiler
323 Purification column condenser

The invention claimed is:

1. A method for producing ethylene oxide, the method comprising:
supplying a raw material gas comprising ethylene, molecular oxygen, and a chlorine compound to an ethylene oxidation reactor;
subjecting the ethylene and the molecular oxygen in the raw material gas to catalytic vapor phase oxidation in the ethylene oxidation reactor in the presence of a silver catalyst, and thereby producing a gas comprising ethylene oxide, water, and a chlorine compound; and
cooling a gas to be cooled comprising the water and the chlorine compound using a heat exchanger,
wherein in the heat exchanger, the gas to be cooled is cooled at a linear gas velocity on the heat exchanger inner tube side of 7 m/s or higher,
wherein the heat exchanger inner tubes are made of stainless steel, and the contents (mass %) of chromium (Cr) and molybdenum (Mo) with respect to the total mass of the stainless steel satisfy the relation of the following Formula 1:

$$11 \leq \text{Content of chromium (mass \%)} + 2 \times \text{content of molybdenum (mass \%)} \leq 18.$$

2. The production method according to claim 1, wherein in the heat exchanger, the temperature at the inlet of the heat exchanger inner tubes is higher than or equal to the dew point of water, and the gas to be cooled is cooled such that the temperature at the outlet of the heat exchanger inner tubes becomes lower than or equal to the dew point of water.

3. The production method according to claim 1, wherein the concentration of the chlorine compound in the raw material gas is from 0.01 ppm by volume to 1,000 ppm by volume based on the volume of the raw material gas.

4. The production method according to claim 1, wherein in the heat exchanger, a heat-absorbing medium for cooling the gas to be cooled is a gas comprising ethylene, molecular oxygen, and a chlorine compound.

5. The production method according to claim 1, wherein the heat exchanger is a multitubular heat exchanger.

6. The production method according to claim 1, wherein the stainless steel is at least one selected from the group consisting of martensitic stainless steels, ferritic stainless steels, austnitic stainless steels and precipitation hardening type stainless steels.

7. A method for producing ethylene oxide, the method comprising:
supplying a raw material gas comprising ethylene, molecular oxygen, and a chlorine compound to an ethylene oxidation reactor;
subjecting the ethylene and the molecular oxygen in the raw material gas to catalytic vapor phase oxidation in the ethylene oxidation reactor in the presence of a silver catalyst, and thereby producing a gas comprising ethylene oxide, water, and a chlorine compound; and
cooling a gas to be cooled comprising the water and the chlorine compound using a heat exchanger,
wherein in the heat exchanger, the gas to be cooled is cooled at a linear gas velocity on the heat exchanger inner tube side of 7 m/s or higher,
wherein the heat exchanger inner tubes are made of stainless steel, and the stainless steel is at least one selected from the group consisting of SUS403, SUS410, SUS410J1, SUS410F2, SUS416, SUS420J1, SUS420J2, SUS420F, SUS420F2, SUS431, SUS440A, SUS440B, SUS440C, SUS440F, SUS405, SUS410L, SUS430, SUS430F, SUS434, SUS201, SUS202, SUS301, SUS302, SUS303, SUS303Se, SUS303Cu, SUS304, SUS304L, SUS304N1, SUS304N2, SUS304LN, SUS304J3, SUS305, SUS309S, SUS321, SUS347, SUS630 and SUS631.

8. The production method according to claim 7, wherein the stainless steel is at least one selected from the group consisting of SUS403, SUS410, SUS410J1, SUS410F2, SUS416, SUS420.11, SUS420J2, SUS420F, SUS420F2, SUS431, SUS405, SUS410L, SUS430, SUS201, SUS301, SUS630 and SUS631.

9. The production method according to claim 7, wherein in the heat exchanger, the temperature at the inlet of the heat exchanger inner tubes is higher than or equal to the dew point of water, and the gas to be cooled is cooled such that the temperature at the outlet of the heat exchanger inner tubes becomes lower than or equal to the dew point of water.

10. The production method according to claim 7, wherein the concentration of the chlorine compound in the raw material gas is from 0.01 ppm by volume to 1,000 ppm by volume based on the volume of the raw material gas.

11. The production method according to claim 7, wherein in the heat exchanger, a heat-absorbing medium for cooling the gas to be cooled is a gas comprising ethylene, molecular oxygen, and a chlorine compound.

12. The production method according to claim 7, wherein the heat exchanger is a multitubular heat exchanger.

* * * * *